United States Patent [19]

Liang

[11] Patent Number: 4,479,002
[45] Date of Patent: Oct. 23, 1984

[54] CARBAMATE-CARBAMOYL FLUORIDE COMPOUNDS

[75] Inventor: Wei C. Liang, So. Charleston, W. Va.

[73] Assignee: Union Carbide Corporation, Danbury, Conn.

[21] Appl. No.: 636,371

[22] Filed: Dec. 1, 1975

[51] Int. Cl.³ ............... C07C 161/00; C07D 213/56; C07D 307/54; C07D 333/24
[52] U.S. Cl. .................. 546/335; 260/453.3; 560/29; 560/134; 260/453.8; 560/148; 260/463; 260/465.4; 424/248.5; 424/248.51; 424/256; 424/263; 424/269; 424/274; 424/275; 424/276; 424/277; 424/278; 424/283; 424/285; 424/300; 546/242; 546/247; 548/541; 549/14; 549/21; 549/28; 549/30; 549/55; 549/65; 549/76; 549/449; 549/452; 549/466; 549/475; 549/496
[58] Field of Search ............ 260/481 C, 347.2, 295 R, 260/332.2 C, 463, 465.4, 294.8 F, 294.8 G; 560/148; 546/335, 242, 247; 549/76, 30, 65, 449, 496, 475; 548/541

[56] References Cited
U.S. PATENT DOCUMENTS
3,812,174 5/1974 Brown et al. .................. 260/481 C Primary Examiner—Vivian Garner
Attorney, Agent, or Firm—C. J. Vicari

[57] ABSTRACT

Carbamate-carbamoyl fluoride compounds are useful intermediates for the production of insecticidal bis-carbamate compounds.

14 Claims, No Drawings

CARBAMATE-CARBAMOYL FLUORIDE COMPOUNDS

This invention relates to a novel class of carbamate-carbamoyl fluoride compounds and to their preparation.

The novel compounds of this invention are compounds corresponding to the following general formula:

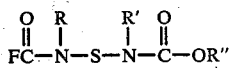

wherein:

R and R' are the same or different and are alkyl groups having from one to four carbon atoms.

R" is a substituted or unsubstituted alkyl, cycloalkyl, phenylalkyl, naphthylalkyl or heterocycloalkyl group wherein the heterocyclic moiety is a five or six member alicyclic ring which includes in any combination, one or two oxygen, sulfur, sulfinyl or sulfonyl groups and which may also include one divalent amino, alkylamino or carbonyl group; wherein the permissible substituents on said groups are one or more halogen, nitrile, alkyl, alkylthio, alkoxy, alkylsulfinyl, alkylsulfonyl, alkoxycarbonyloxyamino, alkylcarbonylamino groups in any combination or R" is alkoxyalkyleneoxyalkyl, alkoxy(dialkyleneoxy)alkyl or alkoxy(trialkyleneoxy)alkyl; with the proviso that except where R" is alkyl, no single alkyl or alkylene moiety in any R" group may include more than six carbon atoms.

Preferred compounds according to this invention are those wherein R and R' are both methyl.

These compounds are useful as intermediates in the preparation of pesticidal compositions by reaction with oxime compounds such as 2-oximino-1,4-dithiane to form bis-carbamate compounds joined by a sulfenyl radical. For example, 2-oximino-1,4-dithiane may be reacted with N-(N'-ethoxycarbonyl-N'-methylaminosulfenyl)-N-methyl carbamoyl fluoride in the presence of an acid acceptor to yield 2[[-O-[N-methyl-N-(N'-methyl-N'-(ethoxycarbonylaminosulfenyl)-carbamoyl)]oximino]]-1,4-dithiane which exhibits outstanding insecticidal and miticidal properties. The preparation and utility of such bis-carbamate compounds, produced by reacting compounds according to this invention with oxime compositions and other active hydrogen containing compounds is more fully described in my copending U.S. patent application Ser. No. 636,623, now U.S. Pat. No. 4,341,795, filed concurrently herewith, entitled "Asymmetrical Bis-Carbamate Compounds."

For example, the compounds of this invention can be reacted with oxime or hydroxyl compounds in accordance with the following reaction scheme:

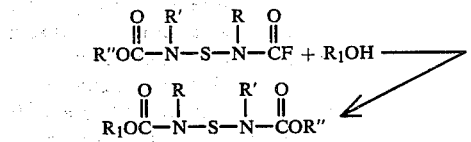

In the above reaction scheme, R, R' and R" are as described above and R₁ is other than R" and in a group of the formula:

naphthyl, benzothienyl, benzofuranyl or:

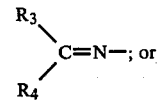

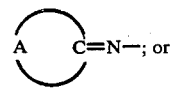

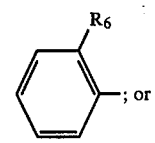

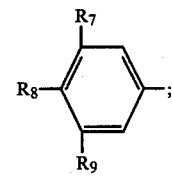

wherein:

R₃ is hydrogen, alkyl, alkylthio or cyano;

R₄ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsufonyl, alkoxy, aminocarbonyl, alkylaminocarbonyl, or dialkylaminocarbonyl groups or R₄ is phenyl, aminocarbonyl, alkylaminocarbonyl, dialkylaminocarbonyl or a R₅CONH— or R₅CON(alkyl)— group, where R₅ is hydrogen, alkyl, alkoxy or alkylthio; and A is a divalent aliphatic chain, completing a five or six member ring, which includes in any combination, one or two oxygen, sulfur, sulfinyl or sulfonyl groups and which may also include one divalent amino, alkylamino or carbonyl group;

R₆ is alkoxy, alkylthio, alkyl, alkylthioalkyl, 2-dioxalanyl or halogen; or

R₇ is alkyl;

R₈ is hydrogen, alkyl, halogen, alkylthio, alkylsulfinyl, alkylsulfonyl, alkoxy, dialkylamino, formylamino, alkylcarbonylamino, alkoxycarbonylamino or dialkylaminomethyleneimino;

R₉ is hydrogen or alkyl; with the proviso that the number of aliphatic carbon atoms in R₃, R₄, A, R₆, R₇, R₈ and R₉, individually, may not exceed eight.

The most pesticidally active compounds that can be prepared from the compounds of this invention are those in which R and R' are methyl. Other compounds that exhibit high levels of pesticidal activity are those in which R₁ is a group of the formula:

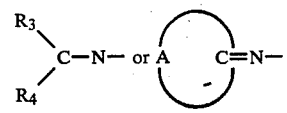

These active compounds exhibit a very high level of pesticidal activity coupled with substantially reduced mammalian toxicity and plant phytotoxicity as compared with other known pesticidal compounds having a comparable spectrum of activity against insect and arachnid pests.

The above reaction is carried out by reacting one equivalent of an oxime ($R_1OH$) with a carbamate-carbamoyl fluoride compound of this invention in the presence of at least one equivalent of an acid acceptor, preferably in an inert solvent to produce the desired assymetrical bis-carbamate compound.

The acid acceptor employed in the above reactions can be either an organic or inorganic base such as triethylamine or sodium or potassium hydroxide. A phase transfer agent such as a crown ether may also be employed. Any conventional inert solvent, such as benzene, toluene, dioxane, tetrahydrofuran, ethylether, methylene chloride or the like can be used in the conduct of these reactions.

These reactions may also be carried out in a two-phase system such as an aqueous solution of an inorganic base as one phase and an aromatic solvent including a quaternary ammonium salt as a phase transfer agent as the second phase. The reaction temperature is not critical in these procedures. The reactions go essentially to completion at room temperature. Elevated temperatures may be employed if it is desired to reduce reaction time. These reactions are preferably carried out at temperatures ranging from 10° to 50° C.

The oxime reactant ($R_1OH$) employed in the procedures described above, is a known class of compounds which can be prepared by conventional methods. See for example U.S. Pat. Nos. 3,752,841; 3,726,908; 3,843,669 and Belgian Pat. Nos. 813,206 and 815,513.

The following examples are provided to more clearly illustrate the manner in which the compounds of this invention can be utilized as intermediates in the preparation of pesticidally active compounds.

EXAMPLE I

Preparation of
S-2-cyanoethyl-N-[[N'-[N"-methyl-N"-(ethoxycarbonyl)aminosulfenyl]-N'-methylcarbamoyloxy]]thioacetimidate To a solution of 5.77 g (0.04 mole) of 2-cyanoethylthio acetaldoxime and 4.45 g (0.044 mole) of triethylamine in 200 ml of 1,4-dioxane was added another solution made up of 8.41 g (0.04 mole) of N-(N'-ethoxycarbonyl-N'-methylaminosulfenyl)-N-methylcarbamoyl fluoride in 30 ml of 1,4-dioxane. The temperature was held at 39° to 43° C. during the addition. The mixture was stirred for 4 hr. and then poured into 400 ml of water. The aqueous mixture was extracted with three portions of 100 ml ethyl acetate. The combined ethyl acetate extracts was washed with 100 ml of saturated aqueous sodium bicarbonate, three 100 ml portions of water, dried over anhydrous magnesium sulfate, filtered and concentrated to give 15 g crude product. Recrystallization from diisopropyl ether gave 9.03 g (68%) of S-2-Cyanoethylthio-N-[[N'-[N"-methyl-N"-(Ethoxycarbonyl)aminosulfenyl]-N'-Methylcarbamoyloxy]]-thioacetimidate, mp 80° to 82° C.

Anal. Calcd for $C_{11}H_{18}N_4O_4S_2$: C, 39.51; H, 5.43; N, 16.75; Found: C, 39.35; H, 5.33; N, 16.62.

EXAMPLE II

Preparation of
2-[O-[N-methyl-N-[N'-methyl-N'-(ethoxycarbonylaminosulfenyl)carbamoyl]oximino]]-1,4-dithiane A solution of 3.0 g (0.02 mole) of 2-oximino-1,4-dithiane, 4.2 g (0.02 mole) of N-(N'-ethoxycarbonyl-N'-methylaminosulfenyl)-N-methyl carbamoyl fluoride and 2.2 g (0.022 mole) of triethylamine in 100 ml of 1,4-dioxane was stirred at ambient temperature for 16 hr. and then poured into 400 ml of water. The aqueous mixture was extracted with three 100 ml portions of ethylacetate and then the ethyl acetate extracts were washed with 100 ml of saturated sodium bicarbonate solution, and then with water until neutral, dried over anhydrous magnesium sulfate, filtered and concentrated to yield 7.0 g residue. Recrystallization from diisopropyl ether gave 5.4 g (80%) of 2-[O-[N-methyl-N-[N'-methyl-N'-(ethoxycarbonylaminosulfenyl)carbamoyl]oximino]]-1,4-dithiane, m.p. 89°–91° C.

Anal. Calcd for $C_{10}H_{17}N_3O_4S_3$: C, 35.38; H, 5.05; N, 12.38; Found: C, 35.47; H, 5.11; N, 12.35.

EXAMPLE III

Preparation of
5-methyl-4-[O-[N-methyl-N-[N'-methyl-N'-(ethoxycarbonylaminosulfenyl)carbamoyl)oximino]]-1,3-oxathiolane A solution 6.66 g (0.05 mole) of 5-methyl-4-oximino-1,3-oxathiolane, 10.5 g (0.05 mole) of N-(N'-ethoxycarbonyl-N'-methylaminosulfenyl)-N-methyl carbamoyl fluoride and 5.57 g (0.055 mole) of triethylamine in 200 ml of 1,4-dioxane was stirred at 42°–45° C. for 2 hr. and at ambient temperature for 16 hr. The mixture was then poured into 400 ml of water and was extracted with four 200 ml portions of ethyl acetate. The combined ethyl acetate extracts were washed with 100 ml of saturated aqueous sodium bicarbonate, then with water until neutral, dried over anhydrous magnesium sulfate, filtered and concentrated to give 15.2 g residue. Recrystallization of the solid residue from diisopropyl ether gave 5.75 g of 5-Methyl-4-[O-[N-Methyl-N-[N'-Methyl-N'-(ethoxycarbonylaminosulfenyl)carbamoyl]oximino]]-1,3-oxathiolane, mp. 54°–56° C.

Anal. Calcd for $C_{10}H_{17}N_3O_5S_2$: C, 37.14; H, 5.30; N, 12.99; Found: C, 37.21; H, 5.31; N, 12.94.

The compounds of Example I, II and III were evaluated to determine their pesticidal activity against two-spotted mite (*Tetranychus urticae* Koch); bean aphid (*Aphis fabae* Scop.); Southern Armyworm (*Prodenia eridania*, (Cram)); Mexican bean beetle (*Epilachna varivestic*, Muls.); and hoursefly (*Musca domestica*, L.).

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being up-righted were considered dead. Aphids remaining on the plants were observed closely for movement and those which were unable to more the length of the body upon stimulation by prodding were considered dead. Percent mortality was recorded for various concentration levels.

Sourthern Armyworm Leaf Spray Bait Test

Larvae of the southern armyworm (*Spodoptera eridania*, (Cram.)), reared on Tendergreen bean plants at a temperature of 80±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig, air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds at the indicated dosage rate against aphid, mite, Southern Armyworm, Bean Beetle and house fly was rated as follows:

A = excellent control
B = partial control
C = inactive or essentially no control at 500 ppm.

The results are summarized in Table I.

TABLE I

| Example | Compound | Aphid | Mite | SAW | MBB | FLY |
|---------|----------|-------|------|-----|-----|-----|
| I | $CH_3\diagdown_{\phantom{x}}C=N-O-\overset{O}{\overset{\|}{C}}-N\diagup^{CH_3}\diagdown_{S-N-\underset{\|}{\underset{O}{C}}-OCH_2CH_3}^{CH_3}$ with $CH_3-S$ | A | B | A | A | A |
| II | $CH_3\diagdown_{\phantom{x}}C=N-O-\overset{O}{\overset{\|}{C}}-N\diagup^{CH_3}\diagdown_{S-N-\underset{\|}{\underset{O}{C}}-O-n-Bu}^{CH_3}$ with $CH_3-S$ | A | B | A | A | A |
| III | $CH_3\diagdown_{\phantom{x}}C=N-O-\overset{O}{\overset{\|}{C}}-N\diagup^{CH_3}\diagdown_{S-N-\underset{\|}{\underset{O}{C}}-O-t-Bu}^{CH_3}$ with $CH_3-S$ | A | C | A | A | A |

The novel compounds of this invention can be prepared in a variety of ways. One method of preparing certain of the compounds of this invention is by the process shown in the following general reaction scheme:

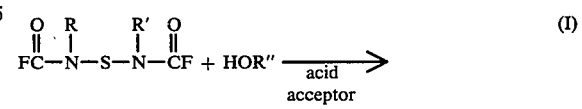
(I)

-continued

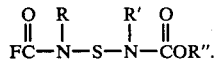

In the above general reaction scheme and those which are described below, R, R' and R" are as defined above.

Another reaction which may be employed for the preparation of compounds according to this invention is shown by the following general reaction scheme:

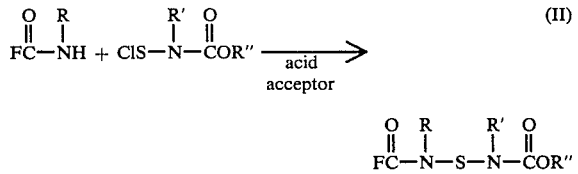

These reactions are conducted in the presence of at least one equivalent of an acid acceptor which may be either an organic or inorganic base such as triethylamine, diazabicyclooctane, pyridine or sodium or potassium hydroxide.

These reactions are also normally conducted in the presence of an inert solvent such as an ether, chlorinated hydrocarbon or aromatic solvent or any of the many inert organic solvents commonly used for such reactions. Illustrative of the inert solvents which may be used are methylene chloride, chloroform, dioxane, tetrahydrofuran, benzene, toluene, acetone, dimethoxyethane, dimethylformamide, acetonitrile and the like.

Reaction temperatures are not critical in the conduct of these reactions and may range from about $-50°$ C. to about $100°$ C. These reactions are preferably conducted at a temperature ranging from about $0°$ C. to about $40°$ C.

The bis-carbamoyl fluoride compounds employed as the starting material in procedure I can be prepared conveniently by reacting hydrogen fluoride and an alkylisocyanate to form N-alkylcarbamoyl fluoride which may then be reacted with sulfur dichloride in the presence of an acid acceptor to produce the desired bis-carbamoyl fluoride compound.

The oxime compounds and chlorosulfenyl compounds employed as starting materials in the procedures described above are known classes of compounds which can be prepared by conventional means. See for example, U.S. Pat. Nos. 3,752,841, 3,726,908, 3,843,669, 3,843,689 and Belgian Pat. Nos. 813,206 and 815,513.

The following representative examples are presented to more clearly illustrate the preparation of the novel compounds of this invention:

EXAMPLE IV

Preparation of N-(N'-ethoxycarbonyl-N'-methylaminosulfenyl)-N-methylcarbamoyl fluoride To a solution of 72.0 g (0.7 mole) of sulfur dichloride in 200 ml of methylene chloride cooled to 0° was added under a nitrogen atmosphere a mixture of 51 g (0.5 mole) of N-methyl ethyl carbamate and 51.0 g (0.5 mole) of triethylamine in 100 ml of methylene chloride over an one hour period, while the temperature was maintained at $-4°$ to $5°$ C. After stirring for 1 hr. at 0° to 5° C. the mixture was filtered and the filtrate was concentrated. Hexanes were used to extract the organic product from the residue which contained a small amount of amine salt. After filtration and concentration 94.0 g of amber oil was obtained.

Anhydrous hydrogen fluoride (10 g, 0.5 mole) was added to 600 ml of methylene chloride at 0° C. in a polyethylene reactor equipped with a stainless steel stirrer and a thermocouple well, and a polyethylene dry ice condenser. Methylisocyanate (28.5 g, 0.5 mole) was added dropwise; the temperature was maintained at $-6°$ to 0° C. After stirring for 1 hour at 0°, to 5° C., a solution of 94 g of N-chlorothio carbamate prepared above in 100 ml of methylene chloride was added to the reaction mixture, followed by a dropwise addition of 51.0 g (0.5 mole) of triethylamine. The mixture was warmed to room temperature. Water was added. After a thorough mixing, layers were separated. The lower organic layer was washed with a saturated aqueous solution of sodium bicarbonate, and then with water until neutral to litmus, dried over anhydrous magnesium sulfate, filtered, and concentrated to give 97.0 g (92%) oily residue. Distillation under reduced pressure yielded 68.4 g of N-(N'-Ethoxycarbonyl-N'-methylaminosulfenyl)-N-methylcarbamoyl fluoride, b.p. 77° C./0.24 mm.

Anal. Calcd. for $C_6H_{11}FN_2O_3S$: C, 34.28; H, 5.28; N, 13.33; Found: C, 34.05; H, 5.13; N, 13.10.

EXAMPLE V

Preparation of N-(N'-n-butoxycarbonyl-N'-methylaminosulfenyl)-N-methylcarbamoyl fluoride To a solution of 45.2 g (0.44 mole) of sulfur dichloride in 200 ml of methylene chloride cooled to $-5°$ C. under a nitrogen atmosphere was added a solution made up of 50.9 g (0.4 mole) of n-butyl N-methylcarbamate, 44.5 g (0.44 mole) of triethylamine and 100 ml of methylene chloride. The addition took 2 hours while the temperature was maintained at $-15°$ C. to 0° C. After stirring for 1 hour the mixture was filtered under a positive nitrogen atmosphere, and the filtrate was concentrated. Solid was removed by extracting the product with hexanes. After filtration the hexane solution was concentrated to give 57.3 g of n-butyl N-chlorothio-N-methylcarbamate.

Anhydrous hydrogen fluoride (8 g, 0.4 mole) was added to 400 ml of methylene chloride at 0° C. in a polyethylene reactor. Methylisocyanate (22.8 g, 0.4 mole) was added at $-5°$ to 0° C. in 0.5 hour. After stirring for one hour at 0° C., a solution of 57.3 g of n-butyl N-chlorothio-N-methylcarbamate in 100 ml of methylene chloride was added to the reaction mixture, followed by a dropwise addition of 40.5 g (0.4 mole) of triethylamine. After warming to room temperature, 300 ml of water was added with vigorous agitation. The lower organic layer was washed with a saturated solution of sodium bicarbonate, then with water until the washings became neutral, dried over anhydrous magnesium sulfate, filtered, and concentrated to give 57.6 g of oily residue. Distillation under reduced pressure gave 32.1 g of N-(N'-n-Butoxycarbonyl-N'-methylaminosulfenyl)-N-methylcarbamoyl fluoride, bp 92° C./0.30 mm.

Anal. Calcd for $C_8H_{15}FN_2O_3S$: C, 40.33; H, 6.35; N, 11.76; Found: C, 39.23; H, 6.46; N, 11.23.

EXAMPLE VI

Preparation of
N-(N'-t-butoxycarbonyl-N'-methylaminosulfenyl)-N-methylcarbamoyl fluoride To a solution of 62 g (0.6 mole) of sulfur dichloride in 200 ml of methylene chloride cooled to 0° C. under a nitrogen atmosphere was added a solution made up of 50.9 g (0.4 mole) of t-butyl N-methylcarbamate, 44.5 g (0.44 mole) of triethylamine and 100 ml of methylene chloride. The temperature was maintained at −2° to 5° C. during the addition. After stirring for one additional hour at 5° C., the mixture was filtered under a positive nitrogen atmosphere, and the filtrate was concentrated. Solid was removed by extracting the product with hexane. After filtration the hexane solution was concentrated to give 81.5 g of t-butyl N-chlorothio-N-methylcarbamate.

Anhydrous hydrogen fluoride (8 g, 0.4 mole) was added to 400 ml of methylene chloride at 0° C. in a polyethylene reactor. Methylisocyanate (22.8 g, 0.4 mole) was added at −10° to 0° C. in 0.5 hour. After stirring for one hour at 0° C., a solution of 81.6 g of t-butyl N-chlorothio-N-methylcarbamate in 100 ml of methylene chloride was added, followed by a dropwise addition of 40.5 g (0.4 mole) of triethylamine. The mixture was allowed to warm to room temperature. Water (300 ml) was added with vigorous agitation. The lower organic layer was washed with a saturated solution of sodium bicarbonate, then with water until the washings became neutral, dried over anhydrous magnesium sulfate, filtered and concentrated to give 86.9 g of oily residue. Distillation under reduced pressure gave 63 g. of N-(N'-t-Butoxycarbonyl-N'-Methylaminosulfenyl)-N-methylcarbamoyl fluoride, bp 82° C./1.25 mm.

Anal. Calcd for $C_8H_{15}FN_2O_3S$: C, 40.33; H, 6.35; N, 11.76; Found: C, 40.04; H, 6.49; N, 11.52.

EXAMPLE VII

Preparation of
N-(N'-2-methoxyethoxycarbonyl-N'-methylaminosulfenyl)-N-methylcarbamoyl fluoride To a solution of 72.0 g (0.7 mole) of sulfur dichloride in 200 ml of methylene chloride cooled to 0° C. under a nitrogen atmosphere was added a solution made up of 66.6 g (0.5 mole) of 2-methoxyethoxy N-methylcarbamate, 55.7 g (0.55 mole) of triethylamine and 100 ml of methylene chloride. The addition took 2.5 hr while the temperature was maintained at −10° to 4° C. After stirring for one additional hour at 5° C., the mixture was filtered under a positive nitrogen atmosphere, and the filtrate was concentrated. Solid was removed by extracting the liquid product into 300 ml of hexanes. After filtration, the hexanes solution was concentrated to give 106.52 g of 2-methoxyethyl N-chlorothio-N-methylcarbamate.

Anhydrous hydrogen fluoride (10.0 g, 0.5 mole) was added to 400 ml of methylene chloride at 0° C. in a polyethylene reactor. Methylisocyanate (28.6 g, 0.5 mole) was added at −10° C. to 0° C. over a 0.5 hr. period. After stirring for one hour at 0° C., a solution of 106.5 g of 2-methoxyethyl N-chlorothio-N-methylcarbamate in 100 ml of methylene chloride was added, followed by a dropwise addition of 50.7 g (0.5 mole) of triethylamine. The mixture was stirred at 0° C. for one more hour. After warming to ambient temperature, 300 ml of water was added and the mixture was stirred vigorously. The organic layer was washed with a saturated aqueous sodium bicarbonate solution, then with water until the washings became neutral, dried over anhydrous magnesium sulfate, filtered and concentrated to give 111 g oily residue. Distillation under reduced pressure gave 74 g (61%) of N-(N'-2-Methoxyethoxycarbonyl-N'-methylaminosulfenyl)-N-methylcarbamoyl fluoride, b.p. 107° C./0.43 mm.

Anal Calcd for $C_7H_{13}FN_2O_4S$: C, 34.99; H, 5.45; N, 11.66; Found: C, 34.82; H, 5.54; N, 11.40.

EXAMPLE VIII

Preparation of
N-(N'-n-dodecycloxycarbonyl-N'-methylaminosulfenyl)-N-methylcarbamoyl fluoride To a solution of 62 g (0.6 mole) of sulfur dichloride in 200 ml of methylene chloride cooled to 0° C. under a nitrogen atmosphere was added a solution made up of 97.4 g (0.4 mole) of n-dodecyl N-methylcarbamate, 44.5 g (0.44 mole) of triethylamine and 150 ml of methylene chloride. The addition took 2.3 hr while the temperature was maintained at −10° to 5° C. After stirring for one additional hour at 5° C. the mixture was filtered under a positive nitrogen atmosphere, and the filtrate was concentrated. Triethylamine hydrochloride was removed by extracting the product into 200 ml of hexane. After filtration, the hexane solution was concentrated to give 125.6 g n-dodecyl N-chlorothio-N-methylcarbamate.

Anhydrous hydrogen fluoride (8 g, 0.4 mole) was added to 400 ml of methylene chloride at 0° C. in a polyethylene reactor. Methylisocyanate (22.8 g, 0.4 mole) was added at −5° C. to 0° C. in 0.5 hr. After stirring for 1 hr at 0° C., a solution of 125.6 g of n-dodecyl N-chlorothio-N-methylcarbamate in 100 ml of methylene chloride was added, followed by a dropwise addition of 40.5 g (0.4 mole) of triethylamine. The mixture was stirred at 0° C. for one hour and was allowed to warm to ambient temperature. Water (300 ml) was added with vigorous stirring. The organic layer was washed with a saturated aqueous solution of sodium bicarbonate, then with water until the washings became neutral, dried over anhydrous magnesium sulfate, filtered and concentrated to give 129 g (92%) of oily N-(N'-n-Dodecyloxycarbonyl-N'-Methylaminosulfenyl)-N-methylcarbamoyl fluoride.

Anal Calcd for $C_{16}H_{31}FN_2O_3S$: C, 54.83; H, 8.92; N, 7.99; Found: C, 55.17; H, 9.09; N, 7.40.

EXAMPLE IX

Preparation of
N-(N'-2-ethylhexyloxycarbonyl-N'-methylaminosulfenyl)-N-methylcarbamoyl fluoride To a solution of 62 g (0.6 mole) of sulfur dichloride in 200 ml of methylene chloride cooled to 0° C. under a nitrogen atmosphere was added a solution of 75 g (0.4 mole) of 2-ethylhexyl N-methylcarbamate and 44.5 g (0.44 mole) of triethylamine in 100 ml of methylene chloride at −10° to 3° C. The addition took 2 hr. After stirring for 1 hr at 5° C., the mixture was filtered under a positive nitrogen atmosphere, and the filtrate was concentrated. The product was extracted into 200 ml of hexanes and the solid triethylamine hydrochloride was filtered. The filtrate was concentrated to give 105.4 g of 2-ethylhexyl N-chlorothio-N-methylcarbamate.

Anhydrous hydrogen fluoride (8 g, 0.4 mole) was added to 400 ml of methylene chloride at 0° C. in a polyethylene reactor. Methylisocyanate (22.8 g (0.4 mole) was added in 0.5 hr at −10° to 0° C. After stirring for 1 hr at 0° C., a solution of 105.4 g of 2-ethylhexyl N-chlorothio-N-methylcarbamate in 100 ml of methylene chloride was added, followed by a dropwise addition of 40.5 g (0.4 mole) of triethylamine. The mixture was stirred at 0° C. for one hour and was allowed to warm to ambient temperature. Water (300 ml) was added with vigorous stirring. The organic layer was washed with a saturated aqueous solution of sodium bicarbonate, then with water until the washings became neutral, dried over anhydrous magnesium sulfate, filtered and concentrated to give 110 g oily residue. Distillation under reduced pressure yielded 77 g (65%) of N-(N′-2-Ethylhexyloxycarbonyl-N′-methylaminosulfenyl)-N-methylcarbamoyl fluoride, bp 130° C./0.5 mm.

Anal. Calcd for $C_{12}H_{23}FN_2O_3S$: C, 48.96; H, 7.87; N, 9.51; Found: C, 49.42; H, 7.60; N, 9.34.

EXAMPLE X

Preparation of N-(N′-benzyloxycarbonyl-N′-methylaminosulfenyl)-N-methylcarbamoyl fluoride To a solution of 46.3 g (0.45 mole) of sulfur dichloride in 200 ml of methylene chloride cooled to 0° C. under a nitrogen atmosphere was added a solution of 49.6 g (0.3 mole) of benzyl N-methylcarbamate and 33.4 g (0.33 mole) of triethylamine in 100 ml of methylene chloride at −6° to 5° C. in 2.3 hr. The mixture was stirred for one additional hour at 0° C. and then filtered under a positive nitrogen atmosphere. The filtrate was concentrated. The product was extracted into 200 ml of hexane and filtered from the triethylamine hydrochloride. The filtrate was concentrated to give 73 g oil.

Anhydrous hydrogen fluoride (6 g, 0.3 mole) was added to 400 ml of methylene chloride at 0° C. in a polyethylene reactor. Methylisocyanate (17.1 g, 0.3 mole) was added in 0.5 hr at −6° to 0° C. After stirring for 1 hr at 0° C., a solution of 73 g of oil prepared above in 100 ml of methylene chloride was added, followed by a dropwise addition of 23.3 g (0.23 mole) of triethylamine. The mixture was stirred at 0° C. for one hour and was allowed to warm up to ambient temperature. Water (300 ml) was added with vigorous agitation. The organic layer was washed with a saturated aqueous solution of sodium bicarbonate, then with water until the washings became neutral, dried over anhydrous magnesium sulfate, filtered and concentrated to give 73 g residue. Distillation under reduced pressure yielded 34 g (42%) of N-(N′-Benzyloxycarbonyl-N′-Methylaminosulfenyl)-N-Methylcarbamoyl fluoride, bp 152° C./0.55 mm.

Anal. Calcd for $C_{11}H_{13}FN_2O_3S$: C, 48.52; H, 4.81; N, 10.29; Found: C, 48.41; H, 4.87; N, 10.12.

EXAMPLE XI

Preparation of N-[[N′-[2-(2-methoxyethoxy)ethoxycarbonyl]-N′-methylaminosulfenyl]]-N-methylcarbamoyl fluoride To a solution of 46.3 g (0.45 mole) of sulfur dichloride in 200 ml of methylene chloride cooled to 0° C. under a nitrogen atmosphere was added a solution of 53.2 g (0.3 mole) of N-methyl 2(2-methoxyethoxy)ethylcarbamate and 33.4 g (0.33 mole) of triethylamine in 100 ml of methylene chloride at −2° to 4° C. in 2.3 hr. The mixture was stirred for one additional hour at 5° C. and then filtered under a positive nitrogen atmosphere. After the filtrate had been concentrated, 200 ml of hexanes was added to extract the product. Triethylamine hydrochloride was filtered and the filtrate was concentrated to give an oily product.

Anhydrous hydrogen fluoride (6.0 g, 0.3 mole) was added to 400 ml of methylene chloride at 0° C. in a polyethylene reactor. Methylisocyanate (17.1 g, 0.3 mole) was added in 0.5 hr. at −7° C. to 0° C. After stirring for 1 hr at 0° C., a solution of the oily intermediate prepared above in 100 ml of methylene chloride was added, followed by a dropwise addition of 30.4 g (0.3 mole) of triethylamine. The mixture was stirred at 0° C. for 1 hr and was allowed to warm up to ambient temperature. Water (300 ml) was added with vigorous agitation. The aqueous layer was saturated with sodium chloride and the organic layer was washed with a saturated aqueous solution of sodium bicarbonate, twice with a saturated sodium chloride solution, dried over anhydrous magnesium sulfate, filtered, and concentrated to give 77 g (90%) of oily N-[[N′-[2-(2-methoxyethoxy)ethoxycarbonyl]-N′-methylaminosulfenyl]]-N-methylcarbamoyl fluoride.

Anal. Calcd for $C_9H_{17}FN_2O_5S$: C, 38.02; H, 6.03; N, 9.85; Found: C, 37.59; H, 6.16; N, 8.96.

EXAMPLE XII

Preparation of N-[N′-(1-methyl-2-methoxyethoxycarbonyl)-N′-methylaminosulfenyl]-N-methylcarbamoyl fluoride To a solution of 61.7 g (0.6 mole) of sulfur dichloride in 200 ml of methylene chloride cooled to 0° C. under a nitrogen atmosphere was added a solution of 58.9 g (0.4 mole) of N-methyl 1-methyl-2-methoxyethyl carbamate and 44.5 g (0.44 mole) of triethylamine in 100 ml of methylene chloride at −8° to 0° C. in 2 hr. The mixture was stirred for one additional hr. at 0°–5° C. and then filtered under a positive nitrogen atmosphere. After the filtrate had been concentrated, 200 ml of hexanes was added to extract the product. Triethylamine hydrochloride was filtered and the filtrate was concentrated to give 90 g of oily intermediate.

Anhydrous hydrogen fluoride (8 g, 0.4 mole) was added to 400 ml of methylene chloride at 0° C. in a polyethylene reactor. Methylisocyanate (22.8 g, 0.4 mole) was added at −5° to 0° C. in 0.5 hr. After stirring for 1 hr. at 0° C., a solution of 90 g of the above oily intermediate in 100 ml of methylene chloride was added, followed by a dropwise addition of 40.5 g (0.4 mole) of triethylamine. The mixture was stirred at 0° C. for 1 hr, and was allowed to warm up to ambient temperature. Water (300 ml) was added while the mixture was vigorously agitated. The aqueous layer was saturated with sodium chloride, and the organic layer was washed with a saturated aqueous sodium bicarbonate solution, then with saturated sodium chloride solution until neutral, dried over anhydrous magnesium sulfate, filtered and concentrated to give 95 g residue. Distillation under reduced pressure yielded 65.4 g of N-[N′-(1-Methyl-2-Methoxyethoxycarbonyl)-N′-Methylaminosulfenyl]-N-Methylcarbamoyl fluoride, b.p. 95° C./0.2 mm.

Anal. Calcd for $C_8H_{15}FN_2O_4S$: C, 37.79; H, 5.95; N, 11.02; Found: C, 37.60; H, 6.00; N, 10.76.

The following compounds are representative of other compounds within the scope of this invention and which can be prepared by the procedures described above:

N-(N'-Methoxycarbonyl-N'-methylaminosulfenyl)-N-methylcarbamoyl fluoride
N-(N'-Ethoxycarbonyl-N-methylaminosulfenyl)-N-methylcarbamoyl fluoride
N-(N'-n-Butoxycarbonyl-N'-methylaminosulfenyl)-N-methylcarbamoyl fluoride
N-(N'-t-Butoxycarbonyl-N'-methylaminosulfenyl)-N-methylcarbamoyl fluoride
N-(N'-2-Ethylhexyloxycarbonyl-N'-methylaminosulfenyl)-N-methylcarbamoyl fluoride
N-(N'-n-Dodecyloxycarbonyl-N'-methylaminosulfenyl)-N-methylcarbamoyl fluoride
N-(N'-Cyclohexyloxycarbonyl-N'-methylaminosulfenyl)-N-methylcarbamoyl fluoride
N-(N'-Cyclopentyloxycarbonyl-N'-methylaminosulfenyl)-N-methylcarbamoyl fluoride
N-(N'-Benzyloxycarbonyl-N'-methylaminosulfenyl)-N-methylcarbamoyl fluoride
N-(N'-o-Chlorobenzyloxycarbonyl-N'-methylaminosulfenyl)-N-methylcarbamoyl fluoride
N-(N'-m-Chlorobenzyloxycarbonyl-N'-methylaminosulfenyl)-N-methylcarbamoyl fluoride
N-(N'-p-Chlorobenzyloxycarbonyl-N'-methylaminosulfenyl)-N-methylcarbamoyl fluoride
N-(N'-o-Methoxybenzyloxycarbonyl-N'-methylaminosulfenyl)-N-methylcarbamoyl fluoride
N-(N'-m-Methoxybenzyloxycarbonyl-N'-methylaminosulfenyl)-N-methylcarbamoyl fluoride
N-(N'-p-Methoxybenzyloxycarbonyl-N'-methylaminosulfenyl)-N-methylcarbamoyl fluoride
N-(N'-o-Nitrobenzyloxycarbonyl-N'-methylaminosulfenyl)-N-methylcarbamoyl fluoride
N-(N'-m-Nitrobenzyloxycarbonyl-N'-methylaminosulfenyl)-N-methylcarbamoyl fluoride
N-(N'-p-Nitrobenzyloxycarbonyl-N'-methylaminosulfenyl)-N-methylcarbamoyl fluoride
N-(N'-Furfuryloxycarbonyl-N'-methylaminosulfenyl)-N-methylcarbamoyl fluoride
N-(N'-2-Pyridylmethoxycarbonyl-N'-methylaminosulfenyl)-N-methylcarbamoyl fluoride
N-(N'-2-Thiophenemethyloxycarbonyl-N'-methylaminosulfenyl)-N-methylcarbamoyl fluoride
N-(N'-2-Methoxyethyloxycarbonyl-N'-methylaminosulfenyl)-N-methylcarbamoyl fluoride
N-[[N'-2-[2-(2-Methoxyethoxy)ethoxy]ethoxycarbonyl-N'-methylaminosulfenyl]]-N-methylcarbamoyl fluoride
N-[N'-(3,4-Dichlorobenzyloxycarbonyl)-N'-methylaminosulfenyl]-N-methylcarbamoyl fluoride
N-[N'-(3-Methylthiobenzyloxycarbonyl)-N'-methylaminosulfenyl]-methylcarbamoyl fluoride
N-[N'-(2,2,2-Trichloroethoxycarbonyl)-N'-propylaminosulfenyl]-N-methylcarbamoyl fluoride
N-[N'-[2-(N''-Methylacetamido)ethoxycarbonyl]-N'-butylaminosulfenyl]-N-methylcarbamoyl fluoride
N-[N'-(2-cyanoethoxycarbonyl)-N'-ethylaminosulfenyl]-N-methylcarbamoyl fluoride
N-(N'-2-Chloroethoxycarbonyl-N'-methylaminosulfenyl)-N-methylcarbamoyl fluoride
N-(N'-3-Chlorobutoxycarbonyl-N'-methylaminosulfenyl)-N-methylcarbamoyl fluoride
N-(N'-2-Methylthiobutoxycarbonyl-N'-methylaminosulfenyl)-N-methylcarbamoyl fluoride
N-(N'-2-Methylthioethoxycarbonyl-N'-methylaminosulfenyl)-N-methylcarbamoyl fluoride
N-[N'-(2,2,2-Trichloroethoxycarbonyl)-N'-methylaminosulfenyl]-N-methylcarbamoyl fluoride
N-[N'-(2-Methylsulfinylethoxycarbonyl)-N'-methylaminosulfenyl]-N-methylcarbamoyl fluoride
N-[N-(2-methylsulfonylethoxycarbonyl)-N'-methylaminosulfenyl]-N-methylcarbamoyl fluoride
N-(N'-2-Nitroethoxycarbonyl-N'-methylaminosulfenyl)-N-methylcarbamoyl fluoride
N-[N'-(4-t-Butylbenzyloxycarbonyl)-N'-methylaminosulfenyl]-N-methylcarbamoyl fluoride.

What is claimed is:

1. A compound of the formula:

$$\underset{FC-N-S-N-C-OR''}{\overset{O\ \ R\ \ \ \ \ R'\ \ O}{\overset{\|\ \ \ |\ \ \ \ \ |\ \ \|}{}}}$$

wherein:
R and R' are the same or different and are alkyl groups having from one to four carbon atoms,
R'' is a substituted or unsubstituted alkyl, cycloalkyl, phenylalkyl, naphthylalkyl or heterocycloalkyl group wherein the heterocyclic moiety is a five or six member alicyclic ring which includes in any combination, one or two oxygen, sulfur, sulfinyl or sulfonyl groups and which may also include one divalent amino, alkylamino or carbonyl group; wherein the permissible substituents on said groups are one or more halogen, nitrile, alkyl, alkylthio, alkoxy, alkylsulfinyl, alkylsulfonyl, alkoxycarbonyloxylamino, or alkylcarbonylamino groups in any combination or R'' is alkoxyalkyleneoxyalkyl, alkoxy(dialkyleneoxy)alkyl or alkoxy(trialkyleneoxy)alkyl; with the proviso that except where R'' is alkyl, no single alkyl or alkylene moiety in any R'' group may include more than six carbon atoms.

2. A compound according to claim 1 wherein R and R' are methyl.

3. A compound according to claim 1 wherein R'' is a heterocycloalkyl group.

4. A compound according to claim 1 wherein R'' is alkyl.

5. A compound according to claim 1 wherein R'' is phenylalkyl.

6. A compound according to claim 1 wherein R'' is naphthylalkyl.

7. A compound according to claim 1 wherein R'' is alkoxyalkyleneoxyalkyl.

8. A compound according to claim 1 wherein R'' is alkoxy(dialkyleneoxy)alkyl.

9. A compound according to claim 1 wherein R'' is alkoxy(trialkyleneoxy)alkyl.

10. A compound according to claim 1 wherein R'' is substituted alkyl.

11. N-(N'-Ethoxycarbonyl-N'-methylaminosulfenyl)-N-methylcarbamoyl fluoride.

12. N-(N'-2-Methoxyethoxycarbonyl-N'-methylaminosulfenyl)-N-methylcarbamoyl fluoride.

13. N-[N'-(1-Methyl-2-methoxyethoxycarbonyl)-N'-methylaminosulfenyl]-N-methylcarbamoyl fluoride.

14. A compound of the formula $$\underset{FC-N-S-N-C-OR''}{\overset{O\ \ R\ \ \ \ \ R'\ \ O}{\overset{\|\ \ \ |\ \ \ \ \ |\ \ \|}{}}}$$

wherein R and R' are the same or different alkyl groups having from one to four carbon atoms and R'' is alkyl, cycloalkyl, phenylalkyl or naphthylalkyl.

* * * * *

UNITED STATES PATENT AND TRADEMARK OFFICE
CERTIFICATE OF CORRECTION

PATENT NO. : 4,479,002
DATED : October 23, 1984
INVENTOR(S) : Wei C. Liang

It is certified that error appears in the above-identified patent and that said Letters Patent is hereby corrected as shown below:

Column 4, line 2, "hr." should read - - hrs. - -.

Column 4, line 45, " hoursefly" should read - - housefly - -.

Column 5, line 7, " more " should read - - move - -.

Column 5, line 11, "Sourthern" should read - - Southern - -.

Signed and Sealed this

Thirtieth Day of July 1985

[SEAL]

Attest:

DONALD J. QUIGG

*Attesting Officer*     *Acting Commissioner of Patents and Trademarks*